United States Patent [19]

Kondo et al.

[11] Patent Number: 5,223,246

[45] Date of Patent: Jun. 29, 1993

[54] EFFERVESCENT COMPOSITION, ITS PRODUCTION AND USE

[75] Inventors: Sadao Kondo, Kawanishi; Hidehiko Nakano, Kusatsu; Tsuneo Uno, Himeji, all of Japan

[73] Assignees: Takeda Chemical Industries, Ltd., Osaka; Otsuka Pharmaceutical Co., Ltd., Tokyo, both of Japan

[21] Appl. No.: 653,311

[22] Filed: Feb. 11, 1991

[30] Foreign Application Priority Data

Feb. 14, 1990 [JP] Japan ................................ 2-33242

[51] Int. Cl.$^5$ ............................................. A61K 9/46
[52] U.S. Cl. ................................ 424/44; 424/43; 514/350
[58] Field of Search ............................ 424/43, 44

[56] References Cited

U.S. PATENT DOCUMENTS

| | | | |
|---|---|---|---|
| 3,667,929 | 6/1972 | Fleming | 71/67 |
| 4,153,678 | 5/1979 | Quinlan | 424/44 |
| 4,267,164 | 5/1981 | Yeh et al. | 424/44 |
| 5,100,674 | 3/1992 | Ser et al. | 424/466 |

FOREIGN PATENT DOCUMENTS

| | | |
|---|---|---|
| 664197 | 11/1965 | Belgium . |
| 0189114 | 7/1986 | European Pat. Off. . |
| 0190689 | 8/1986 | European Pat. Off. . |
| 0217631 | 4/1987 | European Pat. Off. . |
| 1938709 | 4/1970 | Fed. Rep. of Germany . |
| 2020893 | 11/1970 | Fed. Rep. of Germany . |
| 2213604 | 6/1973 | Fed. Rep. of Germany . |
| 917456 | 2/1963 | United Kingdom . |
| 1055854 | 1/1967 | United Kingdom . |
| 1276839 | 6/1972 | United Kingdom . |
| 1300998 | 12/1972 | United Kingdom . |
| 1370766 | 10/1974 | United Kingdom . |
| 2019844 | 11/1979 | United Kingdom . |
| 2083997 | 4/1982 | United Kingdom . |

Primary Examiner—Allen J. Robinson
Assistant Examiner—Brian M. Burn
Attorney, Agent, or Firm—Wenderoth, Lind & Ponack

[57] ABSTRACT

The present invention provides a water-soluble effervescent composition prepared by hot-melting (i) an active component and (ii) an acid and a carbonate for effervescing, both in powdery or granular state, with (iii) a water-soluble adjuvant whose melting point is not lower than 40° C., for addition to drinking water.

21 Claims, No Drawings

EFFERVESCENT COMPOSITION, ITS PRODUCTION AND USE

FIELD OF THE INVENTION

This invention relates to an effervescent composition and a method of preparing same. More specifically, it relates to an effervescent composition capable of allowing a hardly water-soluble active component to be readily soluble in water, especially to an agent for addition to drinking water.

DESCRIPTION OF THE PRIOR ART

In the operation of livestock breeding, administration of a drug dissolved in drinking water or mixed in feedstuff for the prophylaxis and therapy of diseases of cows, swine, chickens, etc. or for supplement of nutritive components to them has been widely conducted. The volume of a drug fluid to be prepared at one time for administration of the drug dissolved in drinking water is said to be, in general, 10l to 100l. It is very cumbersome and tedious to prepare, by stirring with human power, such a large volume of solution. Therefore, for administering drinking water containing, as the active component, a compound having a low solubility in water and being slow in dissolution rate such as a synthetic antibacterial agent of pyridone carboxylic acid type, preparation of a composition capable of readily dissolving the active component in a short time is strongly required.

On the other hand, in U.S. Pat. No. 4,153,678 and British Patent Application Laid-Open No. 2083997, there are disclosed effervescent tablets for addition to animal drinking water, respectively containing levamisole and vitamins or minerals as active components, and U.S. Pat. No. 3,667,929 discloses that, an effervescent powdery composition coated by pulverizing active components such as piperazine acid salt, copper sulfate or sodium nitrate, an acid substance and carbonate together with a hydrophobic or a slowly dissolving material, is useful as an agent for addition to animal drinking water or a material for horticultural use. These effervescent compositions are, however, not always satisfactory in practical use in respects of dispersibility, disintegrability or rapid dissolution property in water.

SUMMARY OF THE INVENTION

Taking the above-described circumstances into consideration, the present inventors studied diligently and found that an effervescent composition obtained by binding together particles of an active component and an acid and a carbonate for effervescent use, all in finely divided form, with a water-soluble adjuvant to be used as the binder, without forming a continuous phase of the adjuvant, is excellent in dispersibility, disintegrability and rapid dissolution property in water, and dissolves in water with very rapid self-disintegration. The present inventors have further conducted studies and accomplished the present invention.

More specifically, the present invention relates to
(1) A water-soluble effervescent composition comprising (i) an active component, (ii) an acid and a carbonate for effervescing, both in a powdery or granular state, and (iii) a water-soluble adjuvant whose melting point is not lower than 40° C., which forms a discontinuous binder phase, provided that when said active component is also an effervescing acid then said active component may be used as said acid for effervescing, and
(2) a method for preparing the composition described in (1) above, which comprises stirring a mixture of (i) an active component, (ii) an acid and a carbonate for effervescing, both in powdery or granular state, and (iii) a water-soluble adjuvant whose melting point is not lower than 40° C., while heating the mixture at a temperature not lower than the melting point of the adjuvant, and then cooling the mixture to room temperature.

DETAILED DESCRIPTION OF THE INVENTION

As the active component, use is made of any one, preferably a therapeutically active component, whose solubility in water at room temperature, in detail at 15° C. to 25° C., is 0.001% or more, preferably up to 1%, more preferably up to 0.1% at pH range of from 2.0 to 12.0, which is exemplified by synthetic antibacterial agents of hardly water-soluble pyridone-carboxylic acid type such as benofloxacin, nalidixic acid, enoxacin, ofloxacin, amifloxacin, flumequine, tosfloxacin, piromidic acid, pipemidic acid, miloxacin, oxolinic acid, cinoxacin, norfloxacin, ciprofloxacin, pefloxacin, lomefloxacin, enrofloxacin, danofloxacin, binfloxacin, sarafloxacin, ibafloxacin, difloxacin and salts thereof. The active component is used in finely divided form, i.e. powder or granulate so as to increase the dissolution rate. It is preferable to use a finely powdered active component to increase the dissolution rate, more preferably, the active component being capable of allowing not less than 80%, desirably not less than 90% of it to pass through a 100 mesh (150 μm) screen. The amount of active component to be incorporated ranges usually from about 0.1 to 50%, preferably about 1 to 25% by weight based on the effervescent composition, and the ratio may be suitably modified depending on the active component then employed. When the active component is an acid substance capable of effervescing by reaction with carbonate, the active component itself may be used as effervescing acid, and, in this case, an acid for effervescing use as set forth below may be optionally added further.

As the acid for effervescing use, an acid substance having an or more acid dissociation constant $10^{-5}$ or more is preferable, and an acid which is in solid state at room temperatures and shows pH 4.5 or lower when saturated into water at room temperatures or its acid alkali metal salts (e.g. sodium salt, potassium salt, etc.) are generally employed. As the acid for effervescing use, a compound which is not harmful to animals including man is desirably employed, which is exemplified preferably by tartaric acid, citric acid, maleic acid, fumaric acid, malic acid, adipic acid, succinic acid and their alkali hydrogen acid salts. And, even in the case of an acid substance such as phosphoric acid or pyrophosphoric acid which is liquid or in liquid state at room temperature, when their acid alkali metal salts are solid at room temperature, those acid alkali metal salts can be employed as acids for effervescing use. Among the above-mentioned acid substances, those having a relatively large acid dissociation constant ($10^{-3}$ or more) and a small hygroscopicity (critical humidity at 30° C. is 40% RH or more) are preferably employed as acids for effervescing use.

As the carbonate for effervescing use, mention is made of carbonate and hydrogencarbonate (in this specification, carbonate and hydrogencarbonate are generically referred to as carbonate) of potassium, lithium, sodium, ammonium or so, and, among them, sodium carbonate is preferable.

The ratio of the above-mentioned acid and carbonate for effervescing use is determined depending on the pH required for dissolving an active component. When the solubility of the active component increases at the acid side, the pH of the solution is lowered by adding the acid in an amount more than equivalent to a carbonate. In this case, when the pH of the solution was measured in various prescriptions of the effervescent composition of the present invention, even the lowest pH was higher than 2.0. When the solubility of the active component increases at the basic side, the pH of the solution is raised by adding the carbonate in an amount more than equivalent to the acid. In this case, even the highest pH of the solution was lower than 12.0. In either case, the pH near the acid substance immediately after the dissolution is low, while the pH near a carbonate is high. Therefore, in the process of dispersion of these solutions, the water-soluble effervescent composition of this invention disintegrates while generating carbon dioxide gas, and, even when the active component is hardly water-soluble it disperses into water in the state of fine particles and then rapidly dissolves in water. In a case where the solubility of an active component does not depend on pH, the ratio of an acid and a carbonate can be optionally selected.

As the amount of carbonate to be incorporated is proportional to the volume of generating carbon dioxide gas, when it is desired to increase the dissolution rate of an active component, it is necessary to increase the amount of carbonate accordingly, and the amount is usually selected from the range of from about 10 to 70%, preferably from about 20 to 40% by weight based on the effervescent composition.

An acid and a carbonate for effervescing use are used respectively in a powdery or granular state, usually 90% or more of them being capable of passing through a 30 mesh (500 μm) screen. However, in the process of stirring with heating as described later, the particles grow by utilizing crude particles as the nucleus, and, therefore, when it is desired to increase the particle size of the resulting effervescent composition, the average particle size of the acid or the carbonate for effervescing use may be selected from the range of from 30 mesh (500 μm) to 100 mesh (150 μm), accordingly.

As the water-soluble adjuvant, mention is made of, for example, polyethylene glycol, polypropylene glycol, polyoxyethylene-polypropylene copolymer, polyethylene ester, polyethylene sorbitan ester, etc. While melting points of these water-soluble adjuvants usually rise with increase of their molecular weights, preferable ones are those with a melting point of 40° C. or higher, more preferably 40° C. to 90° C., especially 50° C. to 70° C. Among the above-mentioned water-soluble adjuvant, polyethylene glycol is preferable, and that having a molecular weight of about 4,000 to 12,000 is more preferable.

The water-soluble adjuvant may be used in any form such as powder, granules, flakes or heat-molten liquid. While the amount of water-soluble adjuvant to be added may suitably be modified depending on the kinds of components in the effervescent composition or properties of the active components, it is selected usually from the range of from about 5 to 25%, preferably from about 8 to 20%, more preferably from about 10 to 15% by weight based on the effervescent composition. When a water-soluble adjuvant is incorporated in an amount exceeding its optimal one, particles of the resulting effervescent composition tend to grow into ones having a diameter of 2 mm or more, inviting slow dissolution rate when used as, for example, an agent for addition to drinking water.

Into the effervescent composition, besides the above-mentioned active component, the acids and the carbonates for effervescing use and the water soluble adjuvant, there may be added, upon necessity, a bulking filler, a surfactant, a disintegrant, a stabilizer, a coloring agent, a flavor-improving agent, a smell-improving agent, etc.

The effervescent composition of this invention can be produced by, for example, a melt-granulation method as shown below. An active component, an acid and a carbonate for effervescing use and a water-soluble adjuvant (granular, flake-like, powdery or liquid melted by heating) are placed into a mixer whose wall is kept at temperatures higher than the melting point of the adjuvant, then the mixture is stirred with an agitating blade whose rotating speed at the tip is not slower than about 2 m/sec. until the water-soluble adjuvant is melted, followed by cooling the mixture to room temperature to prepare the composition of the present invention.

The effervescent composition of this invention may be any form, but it is preferably in the state of powder or fine particles to increase the dissolution rate, more preferably a particle size such that 90% or more passes a 16 mesh (1,000 μm) screen, especially preferably a particle size such that more than 90% passes a 18 mesh (850 μm) screen.

In the effervescent composition of this invention, an active component and an acid and a carbonate for effervescing use, respectively in finely divided form, are fused with a water-soluble adjuvant. More specifically, since the molten water-soluble adjuvant serves, while not forming a continuous phase but a discontinuous phase, to have the active component and the acid and carbonate for effervescing use, respectively in finely divided form, bound with each other, the cohesiveness between the respective particles when the composition is dissolved in water lowers, resulting in accelerating the dispersibility and disintegrability of the effervescent composition and the dissolution rate thereof. The composition of this invention, which dissolves in water in a short period of time while quite rapidly self-disintegrating, is advantageously used as an agent for addition to drinking water, containing e.g. a synthetic antibacterial agent of pyridone carboxylic acid type having a slow dissolution rate.

EXAMPLES

By the following working examples and experimental examples, the present invention is described more concretely, but is not limited thereto.

Incidentally, the particle sizes of the active components (benofloxacin, ofloxacin, enoxacin, norfloxacin) are all 150 μm or smaller, and the particle sizes of the acids for effervescing use (L-tartaric acid, citric acid, succinic acid) and carbonate (sodium carbonate) are all not larger than 500 μm.

EXAMPLE 1

A glass beaker was charged with 0.5 g of benofloxacin, 3.0 g of L-tartaric acid, 0.9 g of sodium carbonate, 0.4 g of polyethylene glycol 6000 and 5.2 g of granulated sugar, and the mixture was stirred one hundred times with a spatula, and was then put on a hot-plate heated at 70° to 80° C., followed by stirring 200 times in about one minute. The resultant mixture was taken off the hot-plate and cooled to room temperature while stirring to prepare an effervescent composition of benofloxacin whose particle size was not larger than 850 μm (average particle size was 230 μm).

EXAMPLE 2

A 6 liter-capacity super mixer (Kawada Seisakusho) was charged with 10 g of benofloxacin, 60 g of L-tartaric acid, 18 g of sodium carbonate, 20 g of dextrin, 24 g of polyethylene glycol 6000 and 68 g of granulated sugar, and the mixture was stirred at 80° C. for 3 minutes at 1000 rpm. The resultant mixture was put in a polyethylene bag, which was cooled to room temperature while shaking to prepare an effervescent composition of benofloxacin whose particle size was not larger than 850 μm (average particle size was 180 μm).

EXAMPLE 3

A 100 liter-capacity super mixer (Kawada Seisakusho) was charged with 1050 g of benofloxacin, 6303 g of L-tartaric acid, 1890 g of sodium carbonate, 2100 g of dextrin, 2520.5 g of polyethylene glycol 6000, 10.5 g of sunset yellow and 7126 g of granulated sugar. The mixture was stirred at about 85° C. for 15 minutes at 500 rpm, and was put in a 60 liter-capacity V-shape mixer (Inoue Seisakusho), stirred for 10 minutes at room temperature, then cooled. The resultant mixture was sieved with No.18 sieve (850 μm) to prepare an effervescent composition of benofloxacin whose particle size was not larger than 850 μm (average particle size was 360 μm).

EXAMPLE 4

A small glass bottle was charged with 50 mg of ofloxacin, 301 mg of citric acid, 122 mg of sodium carbonate and 26 mg of polyethylene glycol 6000. The mixture was stirred with a spatula 100 times, was then processed in the same manner as Example 1 to prepare an effervescent composition of ofloxacin whose particle size was not larger than 850 μm (average particle size was 250 μm).

EXAMPLE 5

A small glass bottle was charged with 52 mg of enoxacin, 288 mg of succinic acid, 142 mg of sodium carbonate and 25 mg of polyethylene glycol 6000. The mixture was stirred with a spatula 100 times, and was then processed in the same manner as Example 1 to prepare an effervescent composition of enoxacin whose particle size was not larger than 850 μm (average particle size was 210 μm).

EXAMPLE 6

A small glass bottle was charged with 10 mg of norfloxacin, 315 mg of succinic acid, 155 mg of sodium carbonate and 26 mg of polyethylene glycol 6000. The mixture was stirred with a spatula 100 times, and was then processed in the same manner as Example 1 to prepare an effervescent composition of norfloxacin whose particle size was not larger than 850 μm (average particle size was 190 μm).

Experimental Example 1

Two grams of a sample was added, at one stroke, to a glass beaker, the inner diameter being 10.5 cm, containing one liter of water. The beaker was left standing, and the time required for dissolution of the sample was measured at about 25° C.

| Solubility of Effervescent Composition | |
|---|---|
| Sample | Dissolution Time |
| Effervescent Composition of Ex. 1 | 0 min. 30 sec. |
| Effervescent Composition of Ex. 2 | 0 min. 20 sec. |
| Effervescent Composition of Ex. 3 | 0 min. 35 sec. |
| Control Composition[a] of Ex. 1 | 30 min. 00 sec. |

[a]Mixed Powder having the same formulation as Ex. 1 (without melt-granulation process)

Experimental Example 2

To a test tube, the inner diameter being 1.5 cm, containing 20 ml of water, was added at one stroke 0.5 g of a sample. The test tube was left standing, and the solubility of the sample was observed at about 20° C. with the naked eye.

| Dissolving Property of Effervescent Composition | |
|---|---|
| Sample | Dissolving property[b] |
| Effervescent composition of Ex. 4 | ⊚ |
| Effervescent composition of Ex. 5 | ⊚ |
| Effervescent composition of Ex. 6 | ○ |
| Control composition[a] of Ex. 4 | X |
| Control composition[a] of Ex. 5 | X |
| Control composition[a] of Ex. 6 | X |

[a]Mixture of an active component and an acid substance
[b]Evaluation standard of solubility
⊚Completely dissolved and became clear within 5 minutes.
○Substantially dissolved in 5 minutes, and became completely clear in 30 minutes.
X Insolubles or turbidity were obsered even after 30 minutes.

What is claimed is:

1. A water-soluble effervescent composition comprising (i) a pyridone carboxylic acid synthetic antibacterial agent, (ii) an acid having an acid dissociation constant of $10^{-5}$ or more and a carbonate for effervescing, both in a powdery or granular state, and (iii) a water-soluble adjuvant whose melting point is not lower than 40° C., which forms a discontinuous binder phase, wherein the amount of said adjuvant is from about 5 to about 25% by weight based on the weight of said composition, provided that when said antibacterial agent is also an effervescing acid then said active component may be used as said acid for effervescing.

2. The composition as claimed in claim 1, in admixture with drinking water.

3. The composition as claimed in claim 1, 90% or more of which passes through a 16 mesh screen.

4. The composition as claimed in claim 1, in which the solubility of the antibacterial agent in water at room temperature is 0.001% or more at pH 2.0 to 12.0.

5. The composition as claimed in claim 1, wherein the synthetic antibacterial agent is selected from the group consisting of benofloxacin, nalidixic acid, enoxacin, ofloxacin, amifloxacin, flumequine, tosfloxacin, piromidic acid, pipemidic acid, miloxacin, oxolinic acid, cinoxacin, norfloxacin, ciprofloxacin, pefloxacin, lomefloxacin, enrofloxacin, danofloxacin, binfloxacin, difloxacin, sarafloxacin, ibafloxacin, and salts thereof.

6. The composition as claimed in claim 1, wherein the synthetic antibacterial agent is selected from the group consisting of benofloxacin, enoxacin, ofloxacin, norfloxacin and salts thereof.

7. The composition as claimed in claim 1, wherein the acid for effervescing is an acid which is solid at room temperature and shows pH 4.5 or lower when saturated into water at room temperature, or its acid alkali metal salt.

8. The composition as claimed in claim 1, wherein the acid for effervescing is selected from the group consisting of tartaric acid, citric acid, maleic acid, fumaric acid, malic acid, adipic acid, succinic acid and their alkali hydrogen acid salts.

9. The composition as claimed in claim 1, wherein the carbonate for effervescing is a carbonate or a hydrogencarbonate of lithium, sodium, potassium or ammonium.

10. The composition as claimed in claim 1, wherein the water-soluble adjuvant is selected from the group consisting of polyethylene glycol, polypropylene glycol, polyoxyethylene-polypropylene copolymer, polyethylene ester and polyethylene sorbitan ester.

11. The composition as claimed in claim 1, wherein the melting point of the water-soluble adjuvant is 40° to 90° C.

12. The composition as claimed in claim 1, wherein the water-soluble adjuvant is polyethylene glycol having a molecular weight of about 4,000 to 12,000.

13. The composition as claimed in claim 1, which comprises about 0.1 to 50% by weight of the antibacterial agent, about 10 to 70% by weight of the carbonate for effervescing, an effective amount of the acid for effervescing to make a solution of the composition with a pH of about 2.0 to 12.0 and about 5 to 25% by weight of the water-soluble adjuvant, based on the weight of the composition.

14. The composition as claimed in claim 1, which comprises about 1 to 25% by weight of the antibacterial agent, about 20 to 40% by weight of the carbonate for effervescing, an effective amount of the acid for effervescing to make a solution of the composition with a pH of about 2.0 to 12.0 and about 10 to 15% by weight of the water-soluble adjuvant, based on the weight of the composition.

15. The composition as claimed in claim 1, wherein the antibacterial agent is a finely powdered synthetic antibacterial agent at least 80% of which passes through a 100 mesh screen and whose solubility is 0.001% or more at pH 2.0 to 12.0, the acid for effervescing is an acid at least 90% of which passes through a 30 mesh screen and which has an acid dissociation constant of $10^{-3}$ or more and 40% RH or more critical humidity at 30° C., the carbonate for effervescing is sodium carbonate at least 90% of which passes through a 30 mesh screen and the water-soluble adjuvant has a melting point of 50° to 70° C.

16. The composition as claimed in claim 1, wherein the antibacterial agent is selected from the group consisting of benofloxacin, enoxacin and ofloxacin, the carbonate for effervescing is sodium carbonate, the acid for effervescing is selected from the group consisting of tartaric acid, citric acid, maleic acid and their sodium and potassium salts, and the water-soluble adjuvant is polyethylene glycol having a molecular weight of about 4000 to 12,000.

17. The composition as claimed in claim 1, which comprises benofloxacin, whose particle size is 150 μm or lower, L-tartaric acid whose particle size is 500 μm or lower, sodium carbonate whose particle size is 500 μm or lower, and polyethylene glycol having a molecular weight of about 6000.

18. A method for preparing a water-soluble effervescent composition, which comprises stirring a mixture of (i) a pyridone carboxylic acid synthetic antibacterial agent,(ii) an acid having an acid dissociation of $10^{-5}$ or more and a carbonate for effervescing, both in a powdery or granular state, and (iii) a water-soluble adjuvant whose melting point is not lower than the melting point of the adjuvant, wherein the amount of said adjuvant is from about 5 to about 25% by weight based on the weight of said composition, and cooling the mixture to room temperature.

19. The method as claimed in claim 18, wherein the antibacterial agent is benofloxacin, the acid for effervescing is L-tartaric acid, the carbonate for effervescing is sodium carbonate, and the water-soluble adjuvant is polyethylene glycol having a molecular weight of about 6000.

20. The composition as claimed in claim 1, wherein the amount of the adjuvant is from about 8 to about 20% by weight based on the weight of the composition.

21. The composition as claimed in claim 1, wherein the amount of the adjuvant is from about 10 to about 15% by weight based on the weight of the composition.

* * * * *